(12) United States Patent
Piper

(10) Patent No.: US 6,338,443 B1
(45) Date of Patent: Jan. 15, 2002

(54) HIGH EFFICIENCY MEDICAL NEBULIZER

(75) Inventor: Samuel David Piper, Sacramento, CA (US)

(73) Assignee: Mercury Enterprises, Inc., Clearwater, FL (US)

(*) Notice: Subject to any disclaimer, the term of this patent is extended or adjusted under 35 U.S.C. 154(b) by 0 days.

(21) Appl. No.: 09/592,119

(22) Filed: Jun. 12, 2000

Related U.S. Application Data

(60) Provisional application No. 60/140,275, filed on Jun. 18, 1999.

(51) Int. Cl.7 ............................................. A61M 11/06
(52) U.S. Cl. .................. 239/340; 239/338; 239/124; 239/370; 239/434; 128/200.18; 128/200.21; 261/78.1
(58) Field of Search ................... 239/124, 338, 239/340, 370, 426, 434, 369; 128/200.18, 200.21, 200.14; 261/78.1

(56) References Cited

U.S. PATENT DOCUMENTS

| 3,097,645 | A |   | 7/1963  | Lester |
| 3,744,722 | A |   | 7/1973  | Burns |
| 3,762,409 | A |   | 10/1973 | Lester |
| 4,054,622 | A |   | 10/1977 | Lester |
| 4,333,450 | A |   | 6/1982  | Lester |
| 4,512,341 | A |   | 4/1985  | Lester |
| 4,566,452 | A |   | 1/1986  | Farr |
| 4,588,129 | A |   | 5/1986  | Shanks |
| 4,635,857 | A |   | 1/1987  | Hughes |
| 4,792,097 | A |   | 12/1988 | Kremer, Jr. et al. |
| RE33,642  | E |   | 7/1991  | Lester |
| 5,355,872 | A |   | 10/1994 | Riggs et al. |
| 5,409,170 | A | * | 4/1995  | Burwell et al. ..... 128/200.18 X |
| 5,503,139 | A | * | 4/1996  | McMahon et al. ...... 239/338 X |
| 5,533,501 | A |   | 7/1996  | Denyer |
| 5,579,757 | A | * | 12/1996 | McMahon et al. ..... 128/200.21 |
| 5,687,912 | A |   | 11/1997 | Denyer |

* cited by examiner

*Primary Examiner*—Steven J. Ganey
(74) *Attorney, Agent, or Firm*—Larson & Larson, P.A.; James E. Larson

(57) ABSTRACT

A pneumatic nebulizer that produces a high volume of aerosols for inhalent delivery of medications and other constituencies. High pressure gas formed into a gas jet is passed through a thin choked region of fluid that is entrailed and impinged upon an aerosol amplifier which creates a spray whose aerosol components are directed up through vents to an aerosol outlet for delivery. Larger-sized liquid particles are caused to pool up in a region surrounding the aerosol amplifer and then drip down back into the liquid medication reservoir.

3 Claims, 7 Drawing Sheets

HIGH EFFICIENCY MEDICAL NEBULIZER

CROSS-REFERENCE TO RELATED APPLICATION

This application claims the benefit of U.S. Provisional Application No. 60/140,275, filed Jun. 18, 1999, entitled "High Efficiency Medical Nebulizer".

BACKGROUND OF THE INVENTION

1. Field of the Invention

This invention pertains generally to aerosol generating devices, and more particularly to a high efficiency pneumatic nebulizer, which may be used to deliver medicinal aerosols.

2. Description of the Background Art

Nebulizers of various types have been widely used for inhalation delivery of aerosols containing medication or other constituents to the conductive airways of the lung and the gas exchange regions of the deep lung. Aerosols are relatively stable suspensions of finely divided droplets or solid particles in a gaseous medium, usually in air or oxygen. When inhaled, aerosol particles may be deposited by contact upon the various surfaces of the respiratory tract leading to potential injury, desirable therapeutic action, or planned diagnostic behavior depending on the particular properties of the particles. Inhalable aerosol particles are those with an aerodynamic equivalent diameter between 1 and 5 micrometers.

Due largely to the high permeability of the lung and the copious blood flow, medications depositing in the lung readily enter the blood for action throughout the body, while other medications can directly influence the airway epithelium and effect responses via various airway receptors. Properly generated and formulated aerosols can therefore be helpful in medical treatment. As tracers of airflow or indicators of lung responses, other types of aerosol particles deposited in the lung can also be a valuable diagnostic tool.

A nebulizer produces aerosol of fine particles by breaking a fluid into fine droplets and dispersing them into a flowing stream of gas. The droplet size from a medical nebulizer is considerably smaller than a conventional spray atomizer. Medical nebulizers are designed to convert aqueous solutions or colloidal suspensions to aerosols of fine, inhalable droplets that enter the lungs of a patient during inhalation and are then deposited on the surface of the respiratory airways. Typical pneumatic (compressed gas) medical nebulizers in current use develop approximately 15 to 30 microliters of aerosol per liter of gas in finely divided droplets with volume or mass median diameters in the respirable range of 2 to 4 micrometers.

Medication intended for aerosolization generally consists of a solute (the medication) mixed into a base solution in which the solute may be dissolved. Predominantly water or saline solutions are used with low solute concentrations, typically ranging from 1.0 to 5.0 mg/mL. The delivery of solute to the patient's airway is the primary purpose of a nebulizer. The delivery of solution is usually of minor therapeutic consequence. The output of a medicinal pneumatic nebulizer, carried by a gas, which powers the nebulizer consists of two principal components: vapor, which is solution in gas form without any solute, and small droplets of solution in liquid state which contain a small amount of medicinal solute.

Previously it was generally assumed in the industry that two pneumatic nebulizers having the same gravimetric output, reservoir solute concentration, and gas flow rate, operating under identical conditions would deliver the same amount of solute or medication. The reasoning behind this assumption was that, at the same temperature, both gas streams exiting each nebulizer would have the same percentage of vapor and small droplets, and that each droplet would have a concentration of solute equal to the concentration of the reservoir. This assumption has recently been shown to be false. Large variances in fact exist in medication delivery efficiency between different nebulizers, with nebulizers currently on the market falling at the low end of the possible efficiency spectrum.

The high percentage of vapor among existing nebulizers is the result of internal loss of large particles, which are typically sprayed onto surfaces within the nebulizer. Aerosol production within a pneumatic nebulizer is not a precisely controlled process. Upon production of respirable aerosol within the nebulizer, there are in addition particles created of various others sizes. Of the liquid entrained by a nebulizer jet, typically 1% or less is converted to respirable aerosol particles, which are able to escape the nebulizer. The remaining 99% assume the form of large aerosol particles which are not able to escape the nebulizer (typically>5 $\mu$M) and are sprayed onto the internal surface areas of the nebulizer or eventually fall back into the nebulizer reservoir.

As particles are removed from the air stream of the inside of the nebulizer, solution will evaporate to take its place in the form of vapor. The vapor can come from one of two places: from the wetted surface areas internal to the nebulizer, or from other aerosol particles which are still airborne within the nebulizer. Where the vapor comes from is very important to the performance of the nebulizer. Vapor which comes from other airborne particles within the nebulizer, decreases the size of the particle from which the vapor is emerging, making it more probable that the particle will escape the nebulizer, while at the same time increasing the concentration of solute within the aerosol particle. The result is increased quantity of medicinal solute to the patient. Vapor which is formed by the evaporation of solution deposited on the inside surface of the nebulizer has already deposited its solute onto the nebulizer inside surface resulting in less solute, or medication, being delivered to the patient. Additionally the solution which is evaporated off the inside surfaces of the nebulizer, results in solute adhering to the nebulizer surface where it is lost to the patient permanently.

A typical high performing nebulizer might have an aerosol density exiting the nebulizer of 30 $\mu$L of fluid per Liter of gas. In general, the gas used to drive the nebulizer is air or oxygen, each of which are capable of carrying 22 $\mu$L of water in vapor form per Liter of gas at standard atmospheric conditions. The difference, 8 $\mu$L of fluid per Liter of gas, is the minimum guaranteed amount of aerosol particles that are carrying solute or medication. A large portion of nebulizers currently on the market perform at this low threshold, while the remainder generally operates with only marginal improvement.

Therefore, a need exists for a nebulizer which can provide a high concentration of solute (medication) to the patient by minimizing the vapor which is formed by solution evaporating off the inside walls of the nebulizer and maximizing the amount of vapor which is formed by solution evaporating from other aerosol particles which are still within the nebulizer. The present invention satisfies the need for a high performance nebulizer, while it in addition provides this functionality in a condensed and economically manufactured package.

SUMMARY OF THE INVENTION

The present invention generally pertains to a pneumatic nebulizer that is able to deliver a high concentration of medication aerosol for a wide range of flow rates and reservoir sizes. The invention is ideal for delivery of medication, which is being carried in a solution, because it is able to deliver a higher medication to solution ratio than existing nebulizers.

By way of example and not of limitation, the present invention employs a jet of gas flowing at the speed of sound to entrain and shatter a stream of fluid against a hemispherical aerosol amplifier which is proximal to the jet orifice. The sonic jet of gas produces a vacuum with respect to atmospheric pressure causing fluid in the nebulizer reservoir to be drawn into the jet of gas. The jet of gas and entrained fluid mix forming small droplets (10–100 $\mu$M) which are traveling at a high rate of speed, due to the sonic jet, and are caused to impact on the aerosol amplifier. The aerosol amplifier may be of a variety of shapes provided that it causes the creation of copious amounts of aerosol particles (0–25 $\mu$M). A majority of non-respirable particles are produced which are also too large to escape the nebulizer. After striking the aerosol amplifier, the aerosol stream is still travelling at a high rate of speed. Placed circumferentially around the aerosol amplifier are a number of spray posts which collect the bulk of the spray coming off the aerosol amplifier. The spray posts are wide enough and close enough to each other to cause significant pooling of fluid between them without causing pooling of fluid on the aerosol amplifier. Pooling of liquid between the spray posts is primarily the result of the spray posts being close enough that the surface tension of the liquid tends to fill the gap. The pooled fluid acts as a spray baffle which collects most of the aerosol particles greater than 10 $\mu$M. Aerosol particles smaller than 10 $\mu$M escape by traveling upward between the aerosol amplifier and the posts. Outside the diameter of the perimeter formed by the posts is a containment baffle. The containment baffle is so shaped and positioned to catch large aerosol and spray which may pass through the posts periodically due to sputtering of the fluid build up around the posts. The result is very small wetted surface area. Fluid build up around the spray posts flows down the secondary and returns directly to the fluid reservoir. Minimizing the wetted surface area within the nebulizer is important because it is directly proportional to the rate of vapor which is formed from solution evaporating off of the internal geometry of the nebulizer.

The particles in the 0 to 5 $\mu$M range, which slipped by the posts and the containment baffle, already have a good chance of escaping the nebulizer. The Particles in the 5 to 10 $\mu$M range, which also slipped by the baffling action, provide the means for vapor production while at the same time being shrunk to below 5 $\mu$M, which will also enable them to escape the nebulizer to be delivered to the patient. Maximizing the aerosol surface area within the nebulizer is primarily a matter of maximizing the number of particles. It is well-known that a volume of gas can only hold up to a certain maximum limit of aerosol particles. Nearing the maximum limit the occurrence of aerosol particle collisions and particle merging increases so as to effectively create the limit. An ideal particle size and a corresponding optimized cutoff limit for the post geometry can be determined in accordance with this limit that varies dependent on total nebulizer volume and flowrate (residence time), but particle size is typically about 10 $\mu$M. Producing such a tremendous amount of aerosol, in the range of 0 to 10 $\mu$M, creates a situation wherein the combined surface area of the particles far exceeds the wetted surface area inside the nebulizer such that the vapor exiting the nebulizer is primarily derived from the aerosol particles. The result is a high performance nebulizer that produces a high solute to solution ratio aerosol.

An object of the invention is to provide a pneumatic nebulizer which can deliver high solute to solution ratios.

Another object of the invention is to provide the means to achieve the performance of a large volume nebulizer within the geometry of a small or medium sized nebulizer.

Another object of the invention is to maximize the amount of medication that can be delivered to the patient.

Another object of the invention is to minimize the amount of medication deposited on the inside surfaces of the nebulizer.

Another object of the invention is to baffle out the large aerosol particles directly into fluid flowing into the fluid reservoir.

Another object of the invention is to provide the means to control the particle size of the nebulizer.

Further objects and advantages of the invention will be brought out in the following portions of the specification, wherein, the detailed description is for the purpose of fully disclosing preferred embodiments of the invention without placing limitations thereon.

BRIEF DESCRIPTION OF THE DRAWINGS

The invention will be more fully understood by reference to the following drawings which are for illustrative purposes only.

DESCRIPTION OF THE SPECIFIC EMBODIMENTS

Figure 1:
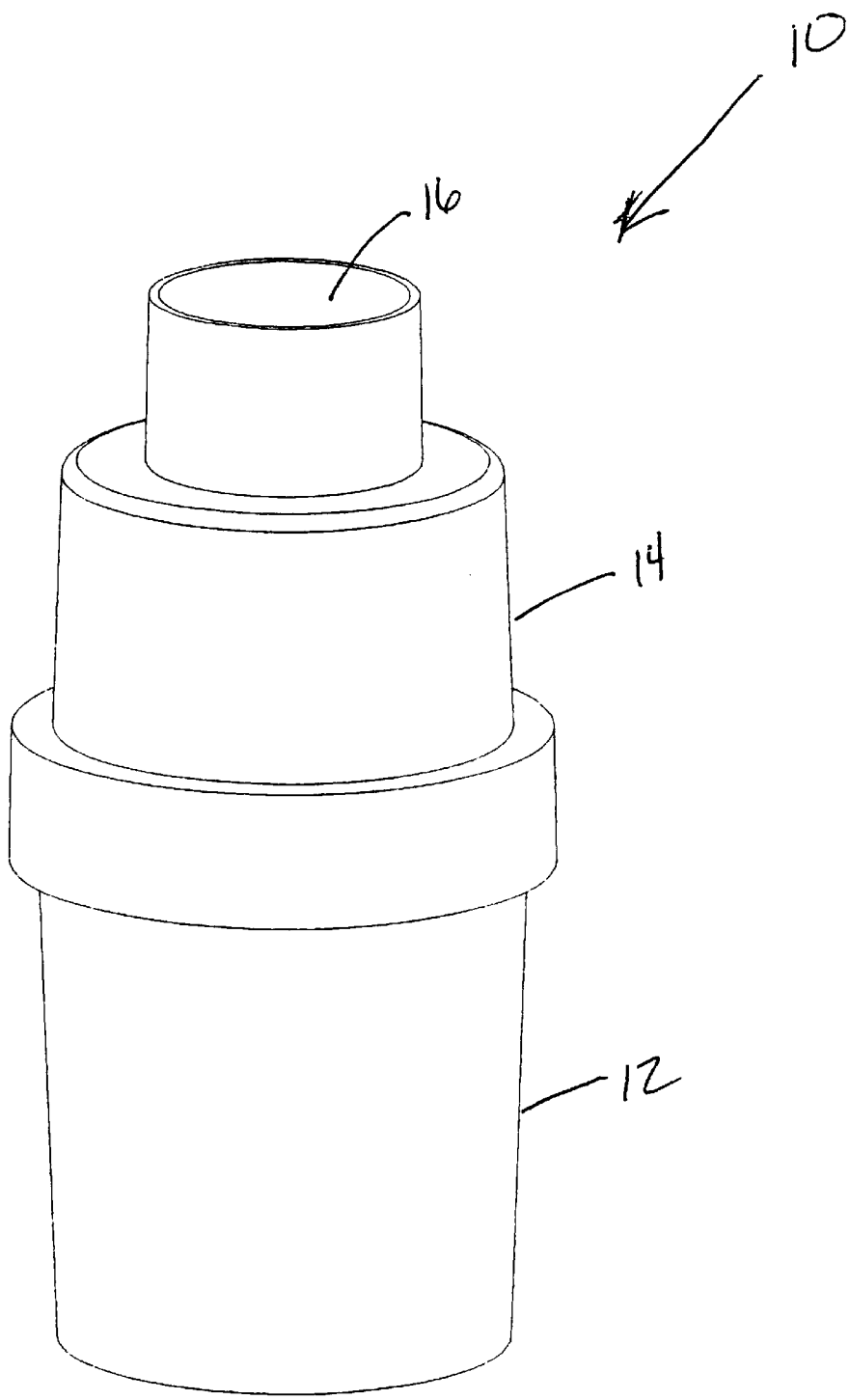
FIG. 1 is a perspective view of a nebulizer according to the invention.

Referring more specifically to the drawings, for illustrative purposes the high efficiency nebulizer of the present invention is embodied in the apparatus generally shown in FIG. 1. It will be appreciated that the apparatus may vary as to configuration and as to details of the parts without departing from the basic concepts as disclosed herein.

Figure 2:
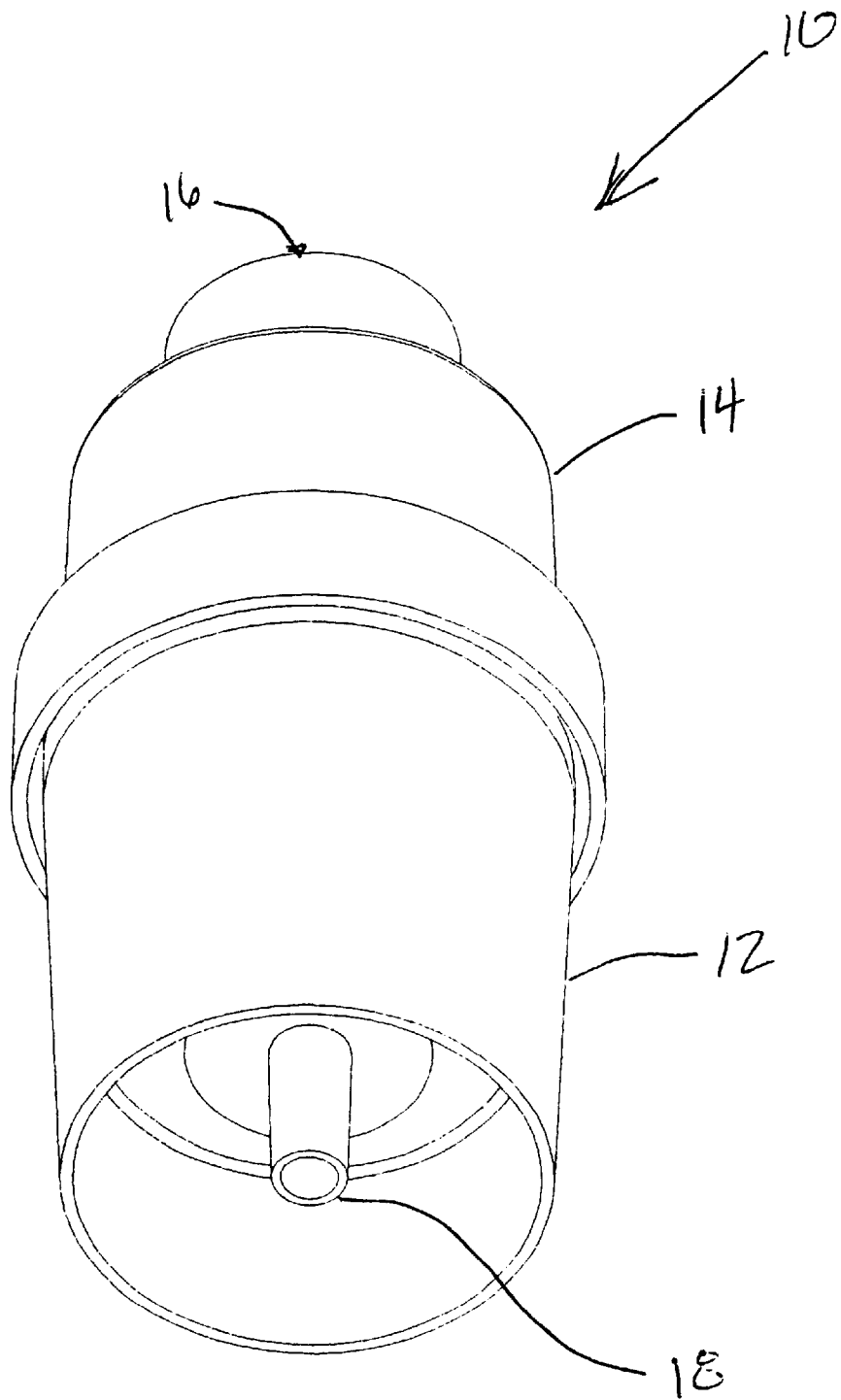
FIG. 2 is a perspective bottom view of the nebulizer of FIG. 1.
Figure 3:
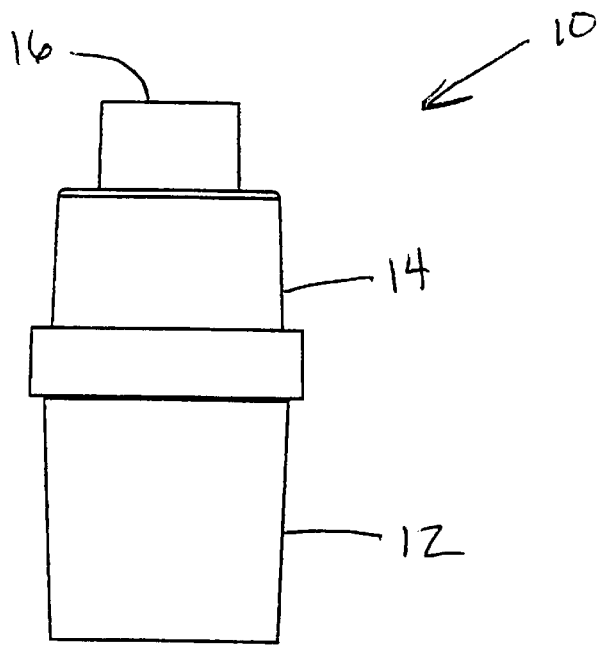
FIG. 3 is an elevation view of the nebulizer.
Figure 4:
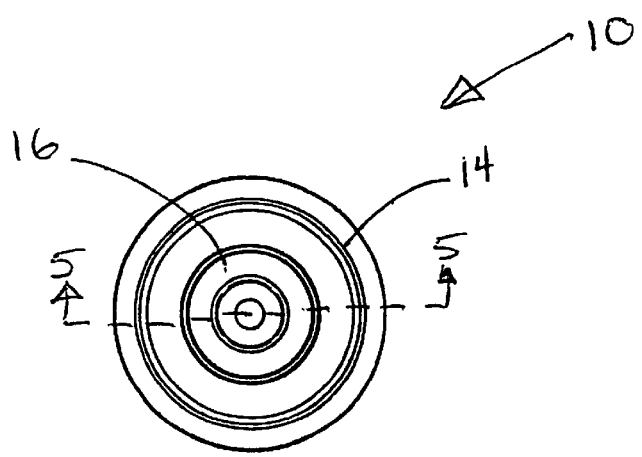
FIG. 4 is a top view of the nebulizer.
Figure 5:
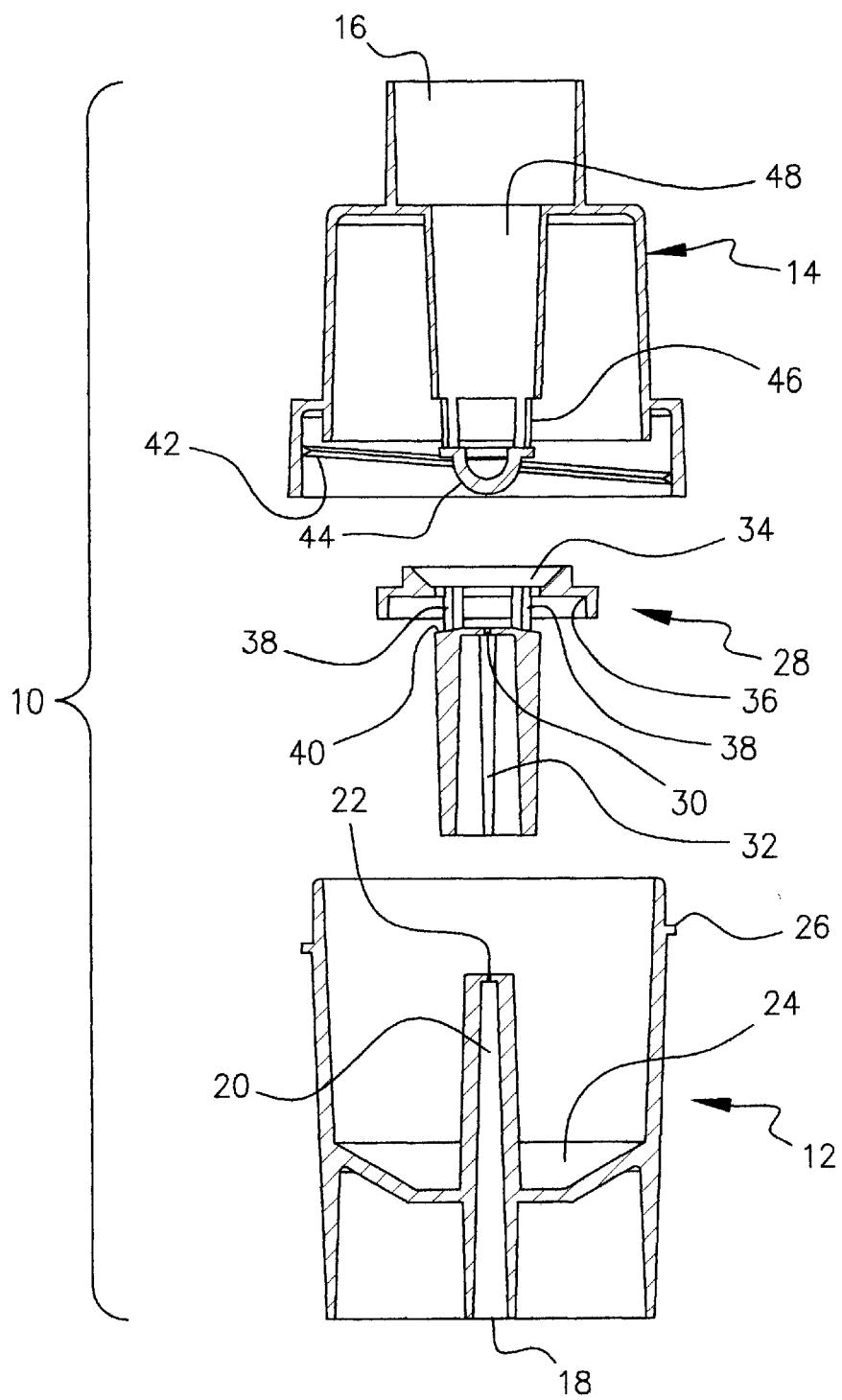
FIG. 5 is an exploded cross-section view of the nebulizer.

Referring to FIG. 1 the nebulizer 10 of the present invention includes a solute jar 12 connected to an inhaler cap 14 that includes an aerosol outlet 16. FIG. 2 depicts the underside of the nebulizer 10 from FIG. 1, with a compressed gas inlet 18. FIG. 3 is side view of the nebulizer. FIG. 4 shows a top view of the nebulizer wherein the barrel of the aerosol outlet 16 is clearly seen. A cross-section of the disassembled structure is shown in FIG. 5 according to the section lines of FIG. 4. The solute jar 12 consists of the compressed gas inlet 18 whose tubular gas passage continues through a gas inlet column 20 that terminates in a primary orifice 22 which forms a gas jet having a gas jet exit plane perpendicularly disposed to the gas jet. The compressed gas jet inlet 18 of the preferred embodiment has a diameter of approximately 0.250" for connection to commonly available compressed gas supply tubing. The solute jar 12 retains the solute in the solute fluid reservoir 24. Solute jar threads 26 are used to engage the inhaler cap 14 for retention during normal operation.

An intermediate section 28 is shown in FIG. 5 for attachment to the gas inlet column of the solute jar 12. The section consists of a secondary orifice 30 at the end of an internal cavity 32 having a gas jet inlet plane and exit plane. On the top of the intermediate section is a dished aerosol amplifier receptacle 34 and an underside containment baffle surface 36 retained atop spray posts 38 on a circular section whose periphery is shaped into a secondary post chamfer 40. Secondary orifice 30 is sized to prevent restriction of the sonic jet flow and to assure that an adequate vacuum is generated. The secondary orifice 30 is typically sized to have a diameter of 2 to 2.5 times greater than primary orifice 22. The length of secondary orifice 30 is typically between 0.020 and 0.050 inches, which has been found to be long enough to allow complete mixing of the sonic jet and the entrained liquid without substantially reducing the speed of the resulting spray. Intermediate section 28 fits onto the gas inlet column 20 of the solute jar 12 by placing the internal cavity 32 over the gas inlet column.

Aerosol inhaler cap 14 is held to the solute jar 12 by engagement of the inhaler cap threads 42 with corresponding solute jar threads 26 of the solute jar. The sonic jet containing solute passing through the primary orifice 22 and secondary orifice 30 is aligned to impinge on a hemispherically shaped aerosol amplifier surface 44. Resultant aerosol passes through aerosol vents 46 into an aerosol passage 48 and up through the aerosol outlet where it may be inhaled.

Figure 6:
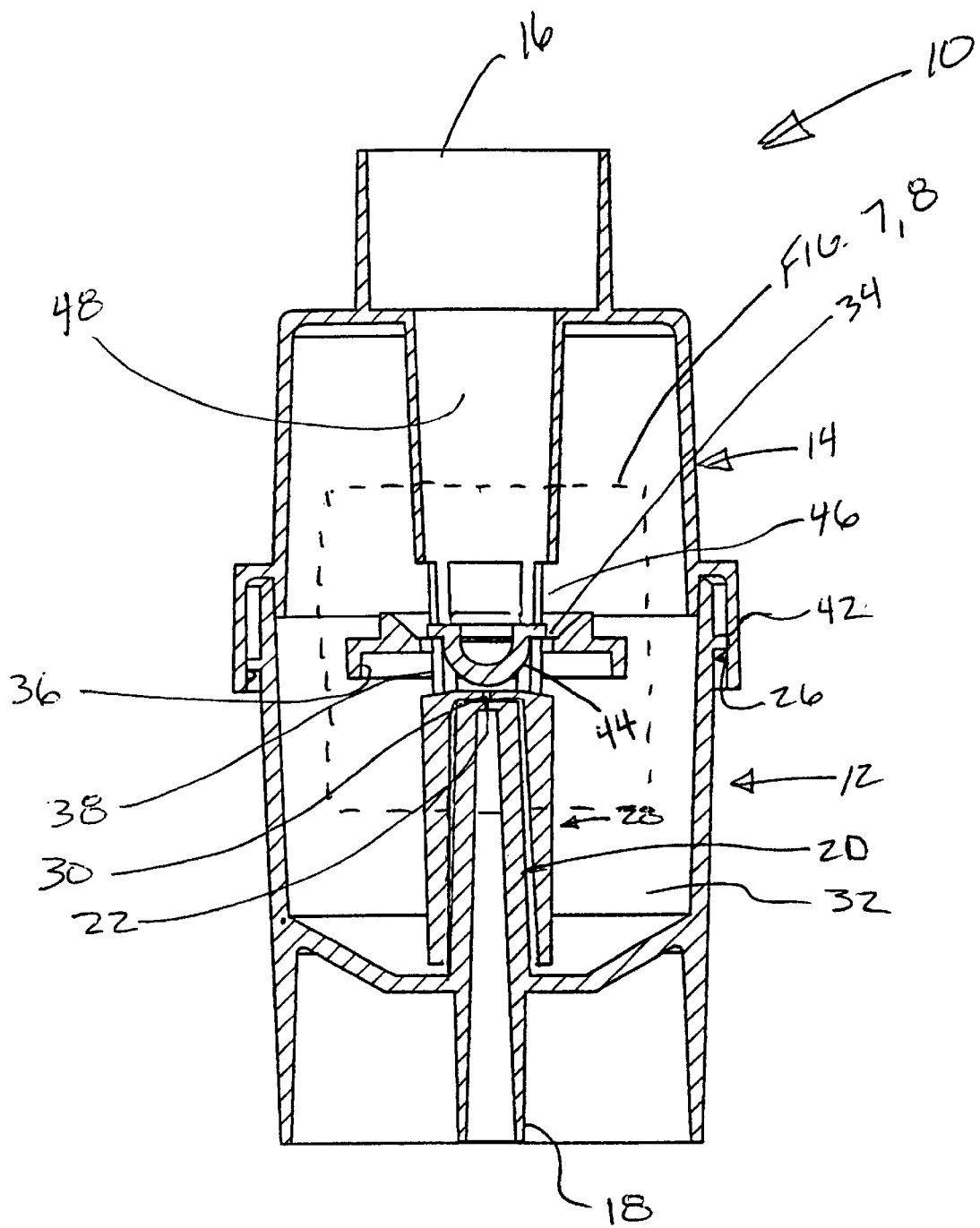
FIG. 6 is an assembled cross-section view of the nebulizer.
Figure 7:
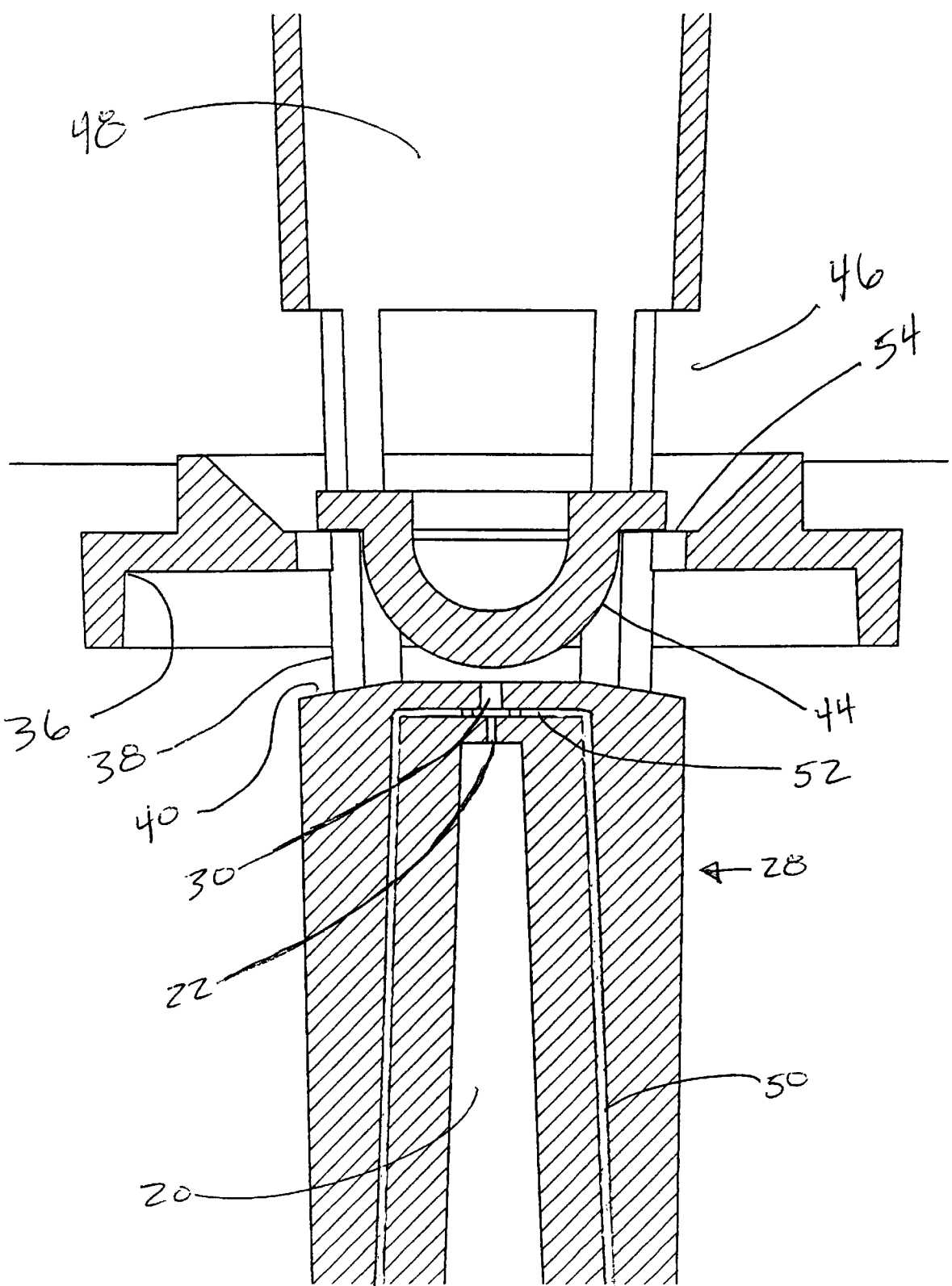
FIG. 7 is a close up cross-section view of the nebulizer orifice region.

In the cross-section of FIG. 6 are shown the assembled sections 12, 14, 28. A central dashed line rectangle of FIG. 6 is shown magnified in the view of FIG. 7. Within FIG. 7, a vertical inter-flow passage 50 and a horizontal fluid choke 52 are formed when the intermediate section 28 and gas inlet column 20 of the solute jar 12 are connected. The sonic jet exiting the primary orifice 22 creates a localized vacuum that entrains liquid from the fluid reservoir to be drawn up through the inter-flow passage 50 and fluid choke 52. The fluid choke 52, containing an inter-orifice gap 53, represents the area of maximum constriction for the passing fluid, and this choke section is made small enough so as to not interfere with the vacuum created by the sonic jet exiting primary orifice 22. The thickness of the circular fluid choke 52 region typically ranges from 0.008 to 0.020", depending on desired rate of liquid entrainment. Assembling the intermediate section 28 over the gas inlet column 20 of the solute jar 12 causes the position of the aerosol amplifier 44 to line up directly over and coincident with the secondary orifice 30, while at the same time creating aerosol passages 54. Aerosol in the 0 to 10 $\mu$M range is allowed to escape up away from the back pressure created by spray posts 38 through the aerosol passages 54. Spray posts 38 are spaced radially around secondary orifice 30 such that spray coming off aerosol amplifier 44 pools up and between spray posts 38. Optimal size and distance between spray posts 38 depends on quantity of liquid entrained in jet, airflow rate, and surface tension of liquid. The preferred embodiment of the present invention has a gas flow rate of 3 L/min with four spray posts 38 of 0.100" width spaced on an inside diameter of 0.400". For the amount of liquid entrained and the gas flow rate, spray posts 38 are spaced close enough to promote a substantial amount of liquid pooling between them while not being spaced so close as to allow pooling of the liquid onto the aerosol amplifier 44, which, in this embodiment, has a diameter of 0.320". Spray posts 38 are positioned on secondary post chamfer 40 which is immediately adjacent to the physical exit plane of secondary orifice 30. Spray post chamfer 40 helps facilitate the pooling of 10 liquid about spray post 38 without accumulating liquid on aerosol amplifier 44. The distance from the exit of secondary orifice 30 and aerosol amplifier 44 can range from 0.01011 to 0.100" depending on speed and shape of jet exiting secondary orifice 30. Containment baffle 36 is so positioned to catch any spray which may escape through spray posts 38 due to sputtering. Containment baffle 36 is shaped so that captured liquid accumulates on the outside diameter where it pools and drips back into the solute fluid reservoir 24.

The primary orifice 22 is the primary means of controlling the pressure-flow relationship of the nebulizer. It is well-known that nebulizers function optimally at the maximum obtainable compressed gas jet velocities. Since most clinical settings have a compressed gas supply which is pressurized to only 50 psig, for nebulizers flows of less than 25 L/min, it is impractical to obtain supersonic flow and a simple orifice with a sonic jet is the optimum design. It is well known from compressible fluid dynamics that any orifice exiting into atmospheric pressures with a supply pressure of 13.7 psig or more will have an exiting jet which reaches sonic velocity, and that the speed may be calculated from the equation $(KRT)_{1/2}$, where K is a gas constant (1.4 for air or oxygen), R is the ideal gas constant, and T is the absolute temperature of the gas. For nebulizers running under normal conditions and having a supply pressure of 13.7 psig or greater, the sonic speed of the jet will be approximately 345 M/sec, regardless of the size of the primary orifice 22. Once a desired compressed gas flow rate has been determined for a specified supply pressure, primary orifice 22 may be sized per the equation $Qm=\rho AV$. Where Qm is the mass flow rate of the gas, $\rho$ is the density of the gas flowing through the primary orifice 22, A is the cross-sectional area of the primary orifice 22, which is the dimension desired, and V is the sonic velocity as calculated above.

Figure 8:
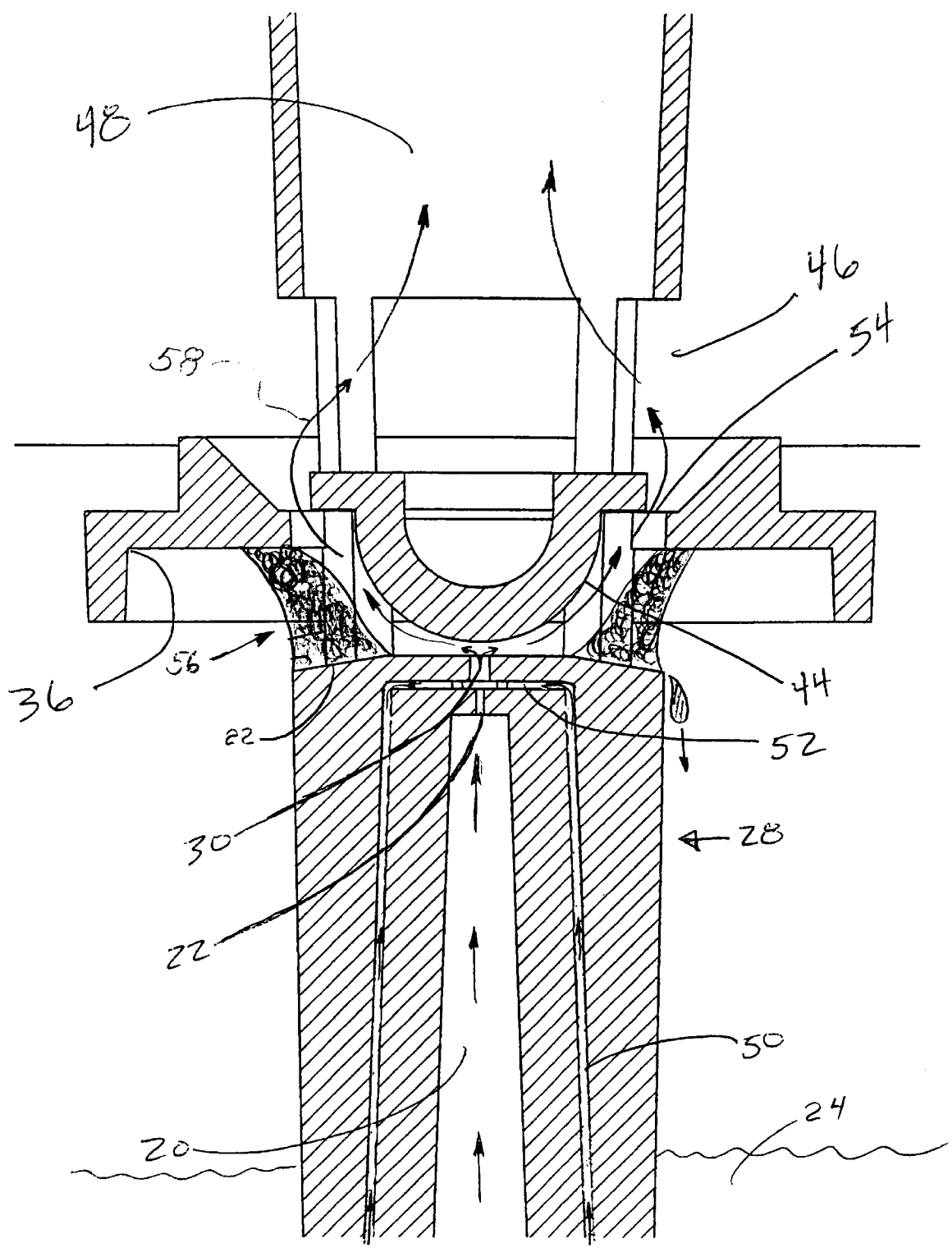
FIG. 8 is a close up cross-section view of the nebulizer orifice region shown with fluid and aerosol flows.

Fluid and aerosol flow within the nebulizer are shown within FIG. 8. Compressed gas at high pressure enters the nebulizer at the compressed gas inlet (not shown) and travels into the gas inlet column 20. At the end of the column the gas is converted to a sonic jet of high speed gas flowing from the primary orifice 22. The gas passes through the fluid choke 52 region that contains a thin region of retained solute. Sonic jet flow creates vacuum that entrains the solution to become entrained in the gas, the combined flow passing out of a secondary orifice 30. As fluid is entrained into the gas jet flow, replacement fluid is drawn up through the inter-flow passage 50 from the solute fluid reservoir 24. Jet flow with entrained fluid flows through a secondary orifice and strikes the curved surface of the aerosol amplifier 44. As the fluid entrained within the jet flow strikes the aerosol amplifier if forms a spray. Larger spray particles are ejected out radially and pool at the spray posts 38 forming accumulated fluids 56. Resultant aerosol particles 58, of a size in the range of 0 to 10 $\mu$M, pass through the aerosol passages 54 and into the large internal cavity formed by the mating of cap 14 and jar 12. Aerosol particles larger than 5 $\mu$M are generally too big to escape the nebulizer without first becoming smaller. It is at this time that the gas carrying the aerosol begins to develop its vapor content.

One aspect of the invention is the recognition that if one were to reduce the amount of liquid deposited on the internal surfaces of nebulizer 2, a greater fraction of the increase in vapor content (primarily water vapor content) of the gas passing through the nebulizer will come from the aerosol particles rather than liquid on the internal surfaces of the nebulizer. The present invention achieves this increase in solute concentration of the resultant aerosol particles by the use of spray posts 38 which, as discussed above, causes the non-aerosolized liquid spray deflected from surface 44 to pool up as accumulated liquid 56 between the posts and drip back down into reservoir 24. Because only a small amount of liquid exists on the internal surfaces of the device, the majority of the vapor content is absorbed from the existing aerosol particles; this reduces the diameters and increases the solute concentration of the resultant aerosol particles. Escaping aerosol and gas travel through aerosol vents 46, up aerosol passage 48, and through the aerosol outlet 16 where it can be delivered to a patient, typically through the use of an attaching mask or other means of patient connection.

The present invention therefore provides a nebulizer which can deliver a high solute to solution ratio aerosol. In this way higher levels of medication can be delivered to a patient with less waste. Although the description above contains many specificities, these should not be construed as limiting the scope of the invention but as merely providing illustrations of some of the presently preferred embodiments of this invention. Thus the scope of this invention should be determined by the patented claims and their legal equivalents.

Any and all patents, applications and printed publications referred to above are incorporated by reference.

What is claimed is:

1. A nebulizer that converts a solution to an aerosol for inhalation delivery of solute medication or other constituencies, comprising:
   (a) a nebulizer housing;
   (b) a compressed gas inlet through which a source of pressurized gas enters the nebulizer;
   (c) at least one orifice through which compressed gas passes from the gas inlet and forms a gas jet;
   (d) a supply of liquid containing solute medication which is entrained into said gas jet to form a spray;
   (e) an aerosol amplifier surface upon which the spray is caused to impinge to form an aerosol containing liquid particles of various sizes;
   (f) multiple spray posts spaced radially around said amplifier surface and said at least one orifice, which cause significant pooling of liquid between said posts around said amplifier surface but are positioned and spaced so as to prevent pooling of liquid on said amplifier surface; and
   (g) said multiple spray posts oriented to allow excess pooling liquid to return to said supply of liquid.

2. A nebulizer made according to claim 1 further comprising an outer containment baffle positioned peripherally about said multiple spray posts, and internal to said nebulizer housing, positioned so as to intercept liquid passing radially outwardly of said multiple spray posts.

3. A nebulizer that converts a solution to an aerosol for inhalation delivery of solute medication or other constituencies, comprising:
   (a) a nebulizer housing;
   (b) a compressed gas inlet through which a source of pressurized gas enters the nebulizer;
   (c) a primary orifice through which compressed gas passes from the gas inlet and forms a gas jet, said primary orifice having a gas jet exit plane defined by a point at which the gas jet leaves the primary orifice, said gas jet exit plane being perpendicular to the direction of the gas jet;
   (d) a secondary orifice aligned axially with said primary orifice, said secondary orifice having a diameter greater than said primary orifice, said secondary orifice having a gas jet inlet plane and a gas jet exit plane;
   (e) said primary orifice gas jet exit plane and said secondary orifice gas jet inlet plane being spaced apart to form an inter-orifice gap which is in liquid communication with a supply of liquid containing solute medication, said gas jet creating a partial vacuum in said inter-orifice gap so that said liquid containing solute medication is caused to be entrained into said inter-orifice gap so said liquid is mixed with said gas jet in said secondary orifice to form a spray which exits said secondary orifice through said gas jet exit plane;
   (f) an aerosol amplifier positioned so said spray impinges thereon to form an aerosol containing liquid particles of various sizes;
   (g) multiple spray posts spaced radially around said amplifier and said secondary orifice, which cause significant pooling of liquid between said posts around said amplifier but are positioned and spaced so as to prevent pooling of liquid on said amplifier;
   (h) said multiple spray posts oriented to allow excess pooling liquid to return to said supply of liquid; and
   (i) an outer containment baffle positioned peripherally about said multiple spray posts and internal to said nebulizer housing, positioned so as to intercept liquid passing radially outwardly of said multiple spray posts.

* * * * *

UNITED STATES PATENT AND TRADEMARK OFFICE
CERTIFICATE OF CORRECTION

PATENT NO. : 6,338,443 B1
DATED : January 15, 2002
INVENTOR(S) : Samuel David Piper It is certified that error appears in the above-identified patent and that said Letters Patent is hereby corrected as shown below:

Title page,
The title page showing the illustrative figure should be deleted and substitute therefore the attached title page.

Drawings,
Figs. 1, 2, 3, 4, 6, 7 and 8, should be replaced with the corrected Figs. 1, 2, 3, 4, 6, 7 and 8, as shown on the attached pages.

Column 6,
Line 5, replace "0.01011 to 0.100"" with -- 0.010" to 0.100" --.

Signed and Sealed this

Twenty-eighth Day of May, 2002

Attest:

JAMES E. ROGAN
Attesting Officer *Director of the United States Patent and Trademark Office*

(12) United States Patent
Piper

(10) Patent No.: US 6,338,443 B1
(45) Date of Patent: Jan. 15, 2002

(54) HIGH EFFICIENCY MEDICAL NEBULIZER

(75) Inventor: Samuel David Piper, Sacramento, CA (US)

(73) Assignee: Mercury Enterprises, Inc., Clearwater, FL (US)

(*) Notice: Subject to any disclaimer, the term of this patent is extended or adjusted under 35 U.S.C. 154(b) by 0 days.

(21) Appl. No.: 09/592,119

(22) Filed: Jun. 12, 2000

Related U.S. Application Data

(60) Provisional application No. 60/140,275, filed on Jun. 18, 1999.

(51) Int. Cl.$^7$ .............................................. A61M 11/06

(52) U.S. Cl. ....................... 239/340; 239/338; 239/124; 239/370; 239/434; 128/200.18; 128/200.21; 261/78.1

(58) Field of Search ................................ 239/124, 338, 239/340, 370, 426, 434, 369; 128/200.18, 200.21, 200.14; 261/78.1

(56) References Cited

U.S. PATENT DOCUMENTS 3,097,645 A 7/1963 Lester
3,744,722 A 7/1973 Burns
3,762,409 A 10/1973 Lester
4,054,622 A 10/1977 Lester
4,333,450 A 6/1982 Lester
4,512,341 A 4/1985 Lester
4,566,452 A 1/1986 Farr
4,588,129 A 5/1986 Shanks
4,635,857 A 1/1987 Hughes
4,792,097 A 12/1988 Kremer, Jr. et al.
RE33,642 E 7/1991 Lester
5,355,872 A 10/1994 Riggs et al.
5,409,170 A * 4/1995 Burwell et al. ..... 128/200.18 X
5,503,139 A * 4/1996 McMahon et al. ...... 239/338 X
5,533,501 A 7/1996 Denyer
5,579,757 A * 12/1996 McMahon et al. ..... 128/200.21
5,687,912 A 11/1997 Denyer

* cited by examiner

*Primary Examiner*—Steven J. Ganey
(74) *Attorney, Agent, or Firm*—Larson & Larson, P.A.; James E. Larson

(57) ABSTRACT

A pneumatic nebulizer that produces a high volume of aerosols for inhalent delivery of medications and other constituencies. High pressure gas formed into a gas jet is passed through a thin choked region of fluid that is entrailed and impinged upon an aerosol amplifier which creates a spray whose aerosol components are directed up through vents to an aerosol outlet for delivery. Larger-sized liquid particles are caused to pool up in a region surrounding the aerosol amplifer and then drip down back into the liquid medication reservoir.

3 Claims, 7 Drawing Sheets

UNITED STATES PATENT AND TRADEMARK OFFICE
CERTIFICATE OF CORRECTION

PATENT NO. : 6,338,443 B1
DATED : January 15, 2002
INVENTOR(S) : Samuel David Piper It is certified that error appears in the above-identified patent and that said Letters Patent is hereby corrected as shown below:

Figure 1 --

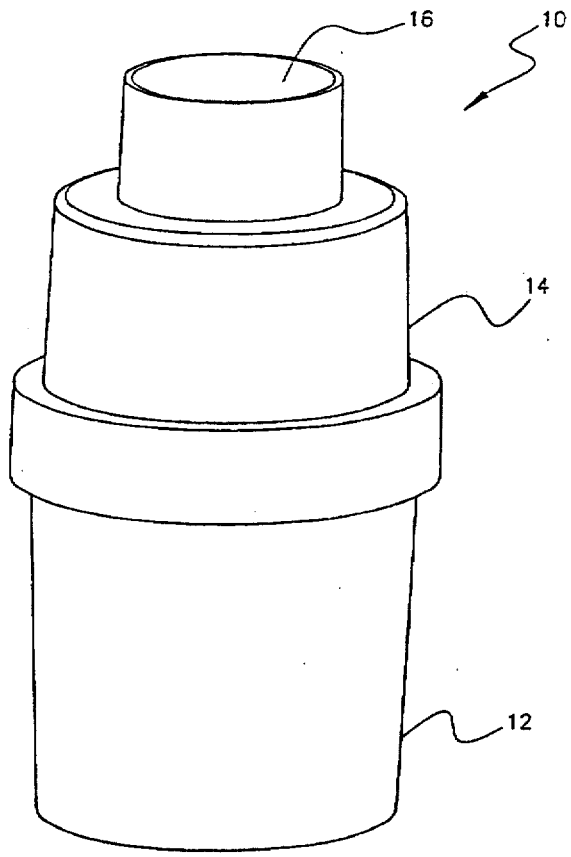

FIG. 1

--

UNITED STATES PATENT AND TRADEMARK OFFICE
CERTIFICATE OF CORRECTION

PATENT NO. : 6,338,443 B1
DATED : January 15, 2002
INVENTOR(S) : Samuel David Piper It is certified that error appears in the above-identified patent and that said Letters Patent is hereby corrected as shown below:

Figure 2 --

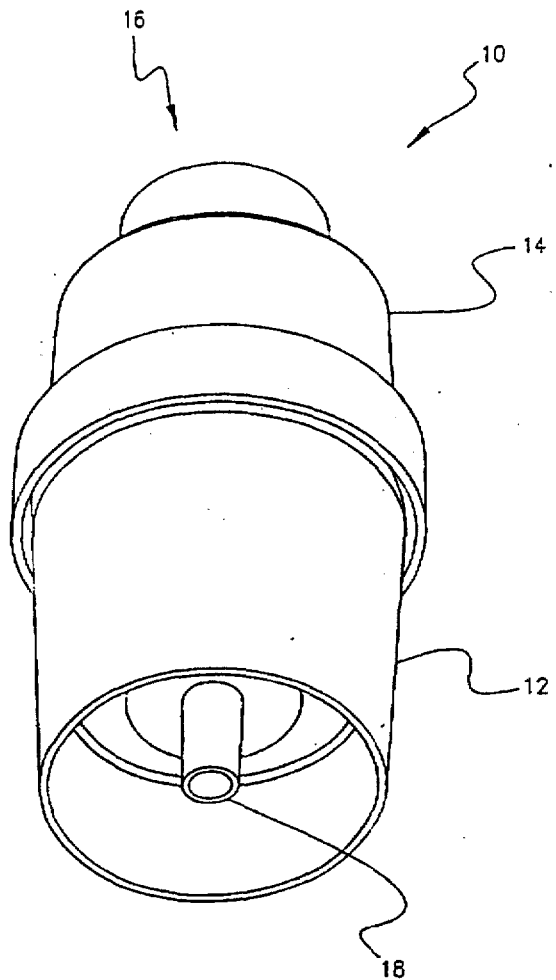

FIG.2

UNITED STATES PATENT AND TRADEMARK OFFICE
CERTIFICATE OF CORRECTION

PATENT NO.    : 6,338,443 B1
DATED         : January 15, 2002
INVENTOR(S)   : Samuel David Piper It is certified that error appears in the above-identified patent and that said Letters Patent is hereby corrected as shown below:

Figure 3 --

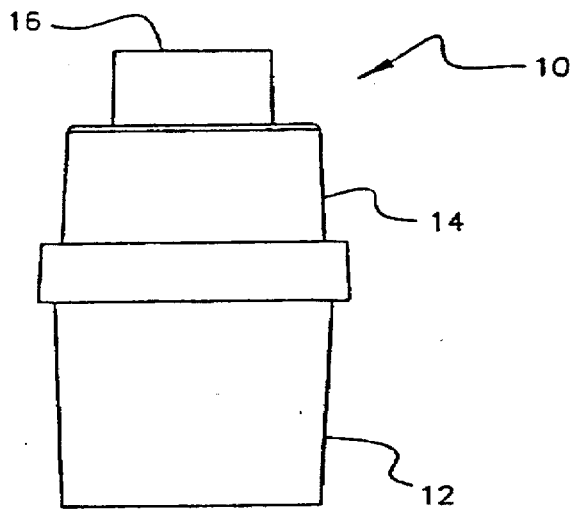

FIG.3

Figure 4 --

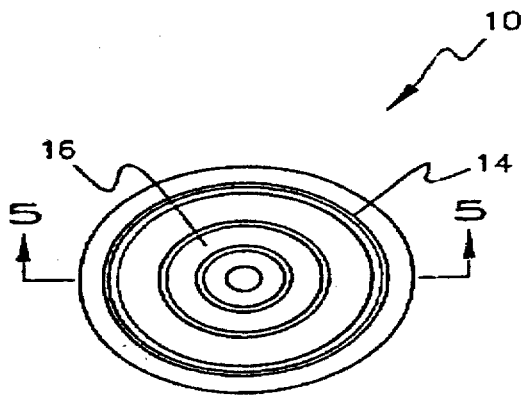

FIG.4

UNITED STATES PATENT AND TRADEMARK OFFICE
CERTIFICATE OF CORRECTION

PATENT NO. : 6,338,443 B1
DATED : January 15, 2002
INVENTOR(S) : Samuel David Piper It is certified that error appears in the above-identified patent and that said Letters Patent is hereby corrected as shown below:

Figure 6 --

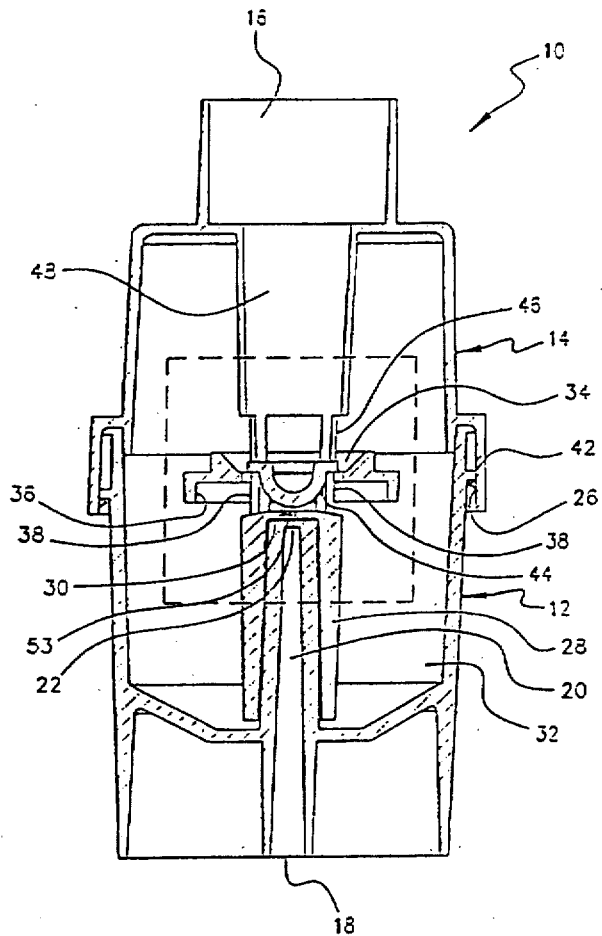

FIG.6

UNITED STATES PATENT AND TRADEMARK OFFICE
CERTIFICATE OF CORRECTION

PATENT NO. : 6,338,443 B1
DATED : January 15, 2002
INVENTOR(S) : Samuel David Piper Page 7 of 8

It is certified that error appears in the above-identified patent and that said Letters Patent is hereby corrected as shown below:

Figure 7 --

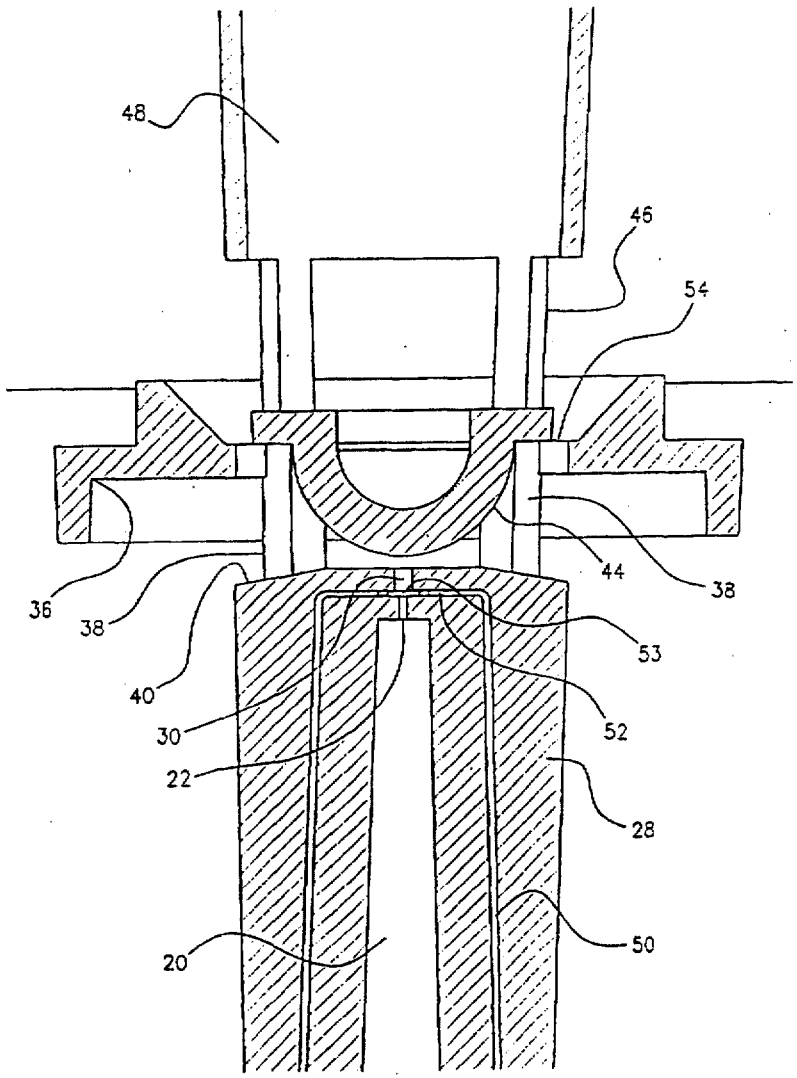

FIG. 7

UNITED STATES PATENT AND TRADEMARK OFFICE
CERTIFICATE OF CORRECTION

PATENT NO. : 6,338,443 B1
DATED : January 15, 2002
INVENTOR(S) : Samuel David Piper It is certified that error appears in the above-identified patent and that said Letters Patent is hereby corrected as shown below:

Figure 8 --

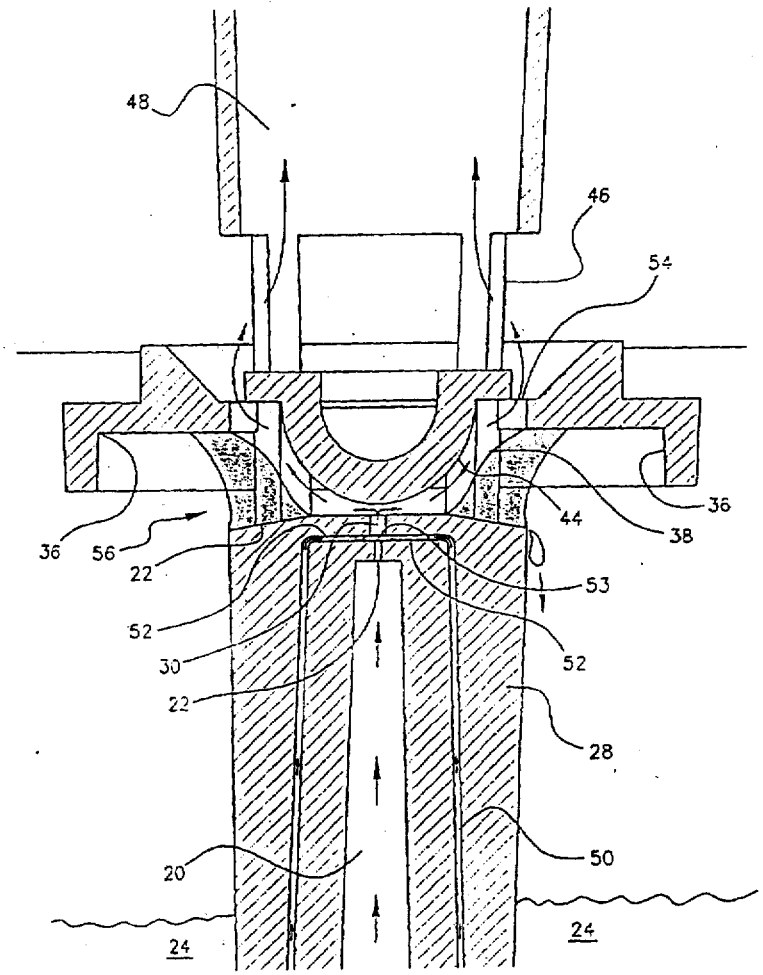

FIG. 8